(12) United States Patent
Enright et al.

(10) Patent No.: US 6,680,058 B1
(45) Date of Patent: *Jan. 20, 2004

(54) COMPOSITIONS AND METHODS FOR CONTRACEPTION IN OR STERILIZATION OF MAMMALS

(75) Inventors: Frederick M. Enright, Baton Rouge, LA (US); Jesse M. Jaynes, Baton Rouge, LA (US); William Hansel, Baton Rouge, LA (US); Patricia A. Melrose, Baton Rouge, LA (US); Philip H. Elzer, Baton Rouge, LA (US)

(73) Assignee: Board of Supervisors of Louisiana State University and Agricultural and Mechanical College, Baton Rouge, LA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/486,143

(22) PCT Filed: Sep. 1, 1998

(86) PCT No.: PCT/US98/18117

§ 371 (c)(1),
(2), (4) Date: Feb. 22, 2000

(87) PCT Pub. No.: WO99/11282

PCT Pub. Date: Mar. 11, 1999

Related U.S. Application Data

(60) Provisional application No. 60/057,456, filed on Sep. 3, 1997.

(51) Int. Cl.[7] .............................................. A61K 38/24
(52) U.S. Cl. .............................. 424/195.11; 424/192.1; 424/184.1; 514/14; 514/841; 514/843
(58) Field of Search ....................... 514/14, 841, 843; 424/195.11, 192.1, 184.1

(56) References Cited

U.S. PATENT DOCUMENTS

| 5,378,688 A | 1/1995 | Nett et al. ................... 514/15 |
| 5,488,036 A | 1/1996 | Nett et al. ................... 514/15 |
| 5,492,893 A | 2/1996 | Nett et al. ................... 514/15 |
| 5,631,007 A | 5/1997 | Ryals et al. ............... 424/94.61 |

FOREIGN PATENT DOCUMENTS

| CA | 2155953 | 9/1994 |
| EP | 0 359 347 | 3/1990 |
| EP | 0 448 511 | 9/1991 |
| WO | WO 83/03971 | 11/1983 |
| WO | WO 86/00090 | 1/1986 |
| WO | WO 90/12866 | 1/1990 |
| WO | WO 90/09799 | 7/1990 |
| WO | WO 93/15751 | 8/1993 |
| WO | WO 94/25616 | 10/1994 |
| WO | WO 96/03519 | 8/1996 |
| WO | WO 97/46259 | 11/1997 |

OTHER PUBLICATIONS

Cho, S. et al., "Evidence for autocrine inhibition of gonadotropin–releasing hormone (GnRH) gene transcription by GnRH in hypothalamic GT1–1 neuronal cells," *Mol. Brain Res.*, vol. 50, pp. 51–58 (1997).

Janaky, T. et al., "Short Chain Analogs of Luteinizing Hormone–Releasing Hormone Containing Cytotoxic Moieties," *Proc. Natl. Acad. Sci. USA*, vol. 89, pp. 10203–10207 (1992).

Lei, Z. et al., "Signaling and transacting factors in the transcriptional inhibition of gonadotropin releasing hormone gene by human chorionic gonadotropin in immortalized hypothalamic GT1–7 neurons," *Mol. & Cell. Endocrinology*, vol. 109, pp. 151–157 (1995).

Morbeck, D. et al., "A Receptor Binding Site Identified in the Region 81–95 of the β–Subunit of Human Luteinizing Hormone (LH) and chorionic gonodatropin (hCG)," *Molecular and Cellular Endocrinology*, vol. 97, pp. 173–181 (1993).

Mores, N. et al, "Activation of LH receptors expressed in GnRH neurons stimulates cyclic AMP production and inhibits pulsatile neuropeptide release," *Endocrinology*, vol. 137, pp. 5731–5734 (1996).

Olson, P. et al., "Endocrine Regulation of the Corpus Luteum of the Bitch as a Potential Target for Altering Fertility," *J. Reprod. Fert. Suppl.*, vol. 39, pp. 27–40 (1989).

Olson, P. et al., "New Developments in Small Animal Population Control," *JAVMA*, vol. 202, pp. 904–909 (1993).

Russell–Jones, G. et al., "Synthesis of LHRH Antagonists Suitable for Oral Administration via the Vitamin $B_{12}$ Uptake System," *Bioconjugate Chem.*, vol. 6, pp. 34–42 (1995).

Sealfon, S. et al., "Molecular mechanisms of ligand interaction with the gonadotropin–releasing hormone receptor," *Endocrine Reviews*, vol. 18, pp. 180–205 (1997).

Albano, C. et al., "Comparison of different doses of gonadotropin–releasing hormone antagonist Cetrorelix during controlled ovarian hyperstimulation," *Fertility and Sterility*, vol. 67, pp. 917–922 (1997).

(List continued on next page.)

*Primary Examiner*—Gary Kunz
*Assistant Examiner*—Fozia Hamud
(74) *Attorney, Agent, or Firm*—John H. Runnels

(57) ABSTRACT

Amphipathic lytic peptides are ideally suited to use in a ligand/cytotoxin combination to induce sterility or long-term contraception in mammals. The peptides act directly on cell membranes, and need not be internalized. Administering a combination of gonadotropin-releasing hormone (GnRH) (or a GnRH agonist) and a membrane-active lytic peptide produces long-term contraception or sterilization in mammals in vivo. The compounds are relatively small, and are not antigenic. Lysis of gonadotropes has been observed to be very rapid (on the order of ten minutes.) The two components—the ligand and the lytic peptide—may optionally be administered as a fusion peptide, or they may be administered separately, with the ligand administered slightly before the lytic peptide, to activate cells with receptors for the ligand, and thereby make those cells susceptible to lysis by the lytic peptide.

39 Claims, No Drawings

OTHER PUBLICATIONS

Conn, P. et al., "Gonadotropin–releasing hormone and its analogues," *New Engl. J. Med.*, vol. 324, pp. 93–103 (1991).

Cornea, A. et al., "Redistribution of $G_{q/11}\alpha$ in the pituitary gonadotrope in response to a gonadotropin–releasing hormone agonist," *Endocrinology*, vol. 139, pp. 397–402 (1998).

Dunn, R.D. et al., "Antigen binding and cytotoxic properties of a recombinant immunotoxin incorporating the lytic peptide, melittin," *Immunotechnology* 2: pp. 229–240 (1996).

Emons, G. et al., "Growth–inhibitory actions of analogues of luteinizing hormone releasing hormone on tumor cells," *Trends in Endocrinology and Metabolism*, vol. 8, pp. 355–362 (1997).

Filicori, M., "Gonadotropin–releasing hormone agonists: a guide to use and selection," *Drugs*, vol. 48, pp. 41–58 (1994).

Garcia–Campayo, V. et al., "Design of stable biologically active recombinant lutropin analogs," *Nature Biotechnology*, vol. 15, pp. 663–667 (1997).

Han, Y. et al., "hCGβ Residues 94–96 alter LH activity without appearing to make key receptor contacts," *Mol. Cell. Endocrin.*, vol. 124, pp. 151–161 (1996).

Hartee, A., "Multiple forms of pituitary and placental gonadotropins," pp. 147–154 in S. Milligan (Ed.), Oxford Reviews of Reproductive Biology (1989).

Janovick, J. et al., "Gonadotropin releasing hormone agonist provokes homologous receptor microaggregation: an early event in seven–transmembrane receptor mediated signaling," *Endocrinology*, vol. 137, pp. 3602–3605 (1996).

Karten, M. et al., "Gonadotropin–releasing hormone analog design. Structure–function studies toward the development of agonists and antagonists: rationale and perspective," *Endocrine Reviews*, vol. 7, pp. 44–66 (1986).

Kovacs, M. et al., "Recovery of pituitary function after treatment with a targeted cytotoxic analog of luteinizing hormone–releasing hormone," *Proc. Natl. Acad. Sci. USA*, vol. 94, pp. 1420–1425 (1997).

Lin, J. et al., "Increased expression of luteinizing hormone/human chorionic gonadotropin receptor gene in human endometrial carcinomas," *J. Clinical Endocrinology & Metabolism*, vol. 79, pp. 1483–1491 (1994).

Maclellan, L. et al., "Superstimulation of ovarian follicular growth with FSH, oocyte recovery, and embryo production from Zebu (*Bos indicus*) calves: Effects of Treatment with a GnRH Agonist or Antagonist," *Theriogenology*, vol. 49, pp. 1317–1329 (1998).

Morbeck, D. et al., "A receptor binding site identified in the region 81–95 of the β–subunit of human luteinizing hormone (LH) and chorionic gonadotropin (hCG)," *Molecular & Cellular Endocrinology*, vol. 97, pp. 173–181 (1993).

Nechushtan, A. et al., "Adenocarcinoma cells are targeted by the new GnRH–$PE_{66}$ chimeric toxin through specific gonadotropin–releasing hormone binding sites," *J. Biol. Chem.*, vol. 298, pp. 11597–11603 (1997).

Puett, D. et al., "The tie that binds: Design of biologically active single–chain human chorionic gonadotropins and a gonadotropin–receptor complex using protein engineering," *Biol. Repro.*, vol. 58, pp. 1337–1342 (1998).

Qayum, A. et al., "The effects of gonadotropin releasing hormone analogues in prostate cancer are mediated through specific tumour receptors," *Br. J. Cancer*, vol. 62, pp. 96–99 (1990).

Sealfon, S. et al., "Molecular mechanisms of ligand interaction with the gonadotropin–releasing hormone receptor," *Endocrine Reviews*, vol. 18, pp. 180–205 (1997).

Sealfon, S. et al., "The gonadotrophin–releasing hormone receptor: structural determinants and regulatory control," *Human Reproduction Update*, vol. 1, pp. 216–230 (1995).

Sugahara, T. et al., "Biosynthesis of a biologically active single peptide chain containing the human common α and chorionic gonadotropin β subunits in tandem," *Proc. Natl. Acad. Sci. USA*, vol. 92, pp. 2041–2045 (1995).

Zalesky, Z. et al, "Ovine luteinizing hormone: Isoforms in the pituitary during the follicular and luteal phases of the estrous cycle and during anestrus," *J. Anim. Sci.*, vol. 70, pp. 3851–3856 (1992).

COMPOSITIONS AND METHODS FOR CONTRACEPTION IN OR STERILIZATION OF MAMMALS

This application is a 371 of PCT/US98/18117, filed on Sep. 1, 1998, which claims the benefit of the Sep. 3, 1997 filing date of provisional application No. 60/057,456 is claimed under 35 U.S.C. §119(e) in the United States.

TECHNICAL FIELD

This invention pertains to compositions and methods for long-term contraception or sterilization of mammals.

BACKGROUND ART

Compositions that have sometimes been used for long-term contraception include those based upon natural or synthetic steroidal hormones to "trick" the female reproductive tract into a "false pregnancy." These steroidal hormones must be administered repeatedly to prevent completion of the estrous cycle and conception. Steroids have side effects that can be potentially dangerous.

P. Olson et al., "Endocrine Regulation of the Corpus Luteum of the Bitch as a Potential Target for Altering Fertility," *J. Reprod. Fert. Suppl.*, vol. 39, pp. 27–40 (1989) discusses the luteal phase and its regulation in bitches. The following discussion appears at page 37: "Specific toxins can be linked to an antibody or hormone and carried to a specific target cell (or cells) which is then killed by the toxin. The idea of developing a 'magic bullet' has been discussed for decades but is now gaining renewed recognition as a potential, highly selective method for destroying specific tissues while leaving other tissues unharmed. For many years it was impossible to develop large quantities of antibodies which would react specifically with only single antigenic determinants. However, with,the advent of monoclonal antibodies, this problem has been largely overcome. Antibodies can be developed to specific hormone receptors (such as the LH receptor) and then coupled to a toxin. All cells with LH receptors should then be destroyed. Although various cell types have not been characterized in dog corpora lutea, destruction of any luteal cell type could potentially result in luteolysis if cell types communicate." (citations omitted)

P. Olson et al., "New Developments in Small Animal Population Control," *JAVMA*, vol. 202, pp. 904–909 (1993) gives an overview of methods for preventing or terminating unwanted pregnancies in small animals. The following discussion appears at page 905: "Tissue-specific cytotoxins—Permanent contraception in females and males might be achieved by administration of a cytotoxin that is linked to gonadotropin-releasing hormone (GnRH) and that selectively destroys gonadotropin-secreting pituitary cells. Similarly, a cytotoxin linked to antibodies against gonadotropin receptors could be targeted to alter gonadal function. Toxins would need to be carefully targeted to specific cells, yet be safe for all other body tissues." (citation omitted).

T. Janaky et al., "Short Chain Analogs of Luteinizing Hormone-Releasing Hormone Containing Cytotoxic Moieties," *Proc. Natl. Acad. Sci. USA*, vol. 89, pp. 10203–10207 (1992) discloses the use of certain hexapeptide and heptapeptide analogs of GnRH as carriers for certain alkylating nitrogen mustards, certain anthraquinone derivatives, antimetabolite, and cisplatin-like platinum complex.

S. Sealfon et al., "Molecular mechanisms of ligand interaction with the gonadotropin-releasing hormone receptor," *Endocrine Reviews*, vol. 18, pp. 180–205 (1997) provides a review of research concerning the interaction between GnRH and its receptor.

D. Morbeck et al., "A Receptor Binding Site Identified in the Region 81–95 of the β-Subunit of Human Luteinizing Hormone (LH) and chorionic gonadotropin (hCG)," *Molecular and Cellular Endocrinology*, vol. 97, pp. 173–181 (1993) disclosed a fifteen amino acid region of LH and hCG that acted as a receptor binding site. (LH and hCG are homologous hormones that produce similar effects.)

S. Cho et al., "Evidence for autocrine inhibition of gonadotropin-releasing hormone (GnRH) gene transcription by GnRH in hypothalamic GT1-1 neuronal cells," *Mol. Brain Res.*, vol. 50, pp. 51–58 (1997) discloses that neuroendocrine populations of GnRH neurons have high affinity receptors for GnRH and for GnRH analogs.

N. Mores et al., "Activation of LH receptors expressed in GnRH neurons stimulates cyclic AMP production and inhibits pulsatile neuropeptide release," *Endocrinology*, vol. 137, pp. 5731–5734 (1996) discloses that LH acts directly on neuroendocrine neurons in the brain See also Z. Lei et al., "Signaling and transacting factors in the transcriptional inhibition of gonadotropin releasing hormone gene by human chorionic gonadotropin in immortalized hypothalamic GT1-7 neurons," *Mol. & Cell. Endocrinology*, vol. 109, pp. 151–157 (1995).

Conventional targeted toxin therapies have several drawbacks. There is a small window for treatment with a particular targeted toxin (on the order of two weeks) before the recipient's immune system mounts an antibody response to the targeted toxin. These antibodies will neutralize the toxin; or worse, may result in the deposition of the toxin in reticuloendothelial tissues (e.g., liver, spleen, lymph nodes, lungs, bone marrow), where they may damage otherwise healthy tissue. Aside from this drawback, the toxin must be internalized by the targeted cell and translocated into the cytoplasm to have effect.

U.S. Pat. Nos. 5,378,688; 5,488,036; and 5,492,893 disclose compounds said to be useful in inducing sterility in mammals. The disclosed compounds were generically described as GnRH (or a GnRH analog) conjugated to a toxin. The toxin was preferably linked to the sixth amino acid of the GnRH agonist. The toxin was preferably one with a translocation domain to facilitate uptake into a cell. The inventors noted that conjugation of the GnRH agonist to the toxin "is necessary because, for the most part, the above toxins, by themselves, are not capable of binding with cell membranes in general. That is to say that applicants have found that it is only when a GnRH analog of the type described herein is linked to a toxin of the type noted above does that toxin become capable of binding to cell membranes . . . " (E.g., U.S. Pat. No. 5,488,036, col. 7, lines 46–52.) The toxins specifically mentioned appear all to have been metabolic toxins, for example ricin, abrin, modeccin, various plant-derived ribosome-inhibiting proteins, pokeweed antiviral protein, α-amanitin, diphtheria toxin, pseudomonas exotoxin, shiga toxin, melphalan, methotrexate, nitrogen mustard, doxorubicin, and daunomycin. None of these toxins is believed to be toxic due to direct interaction with the cell membrane. In the in vivo experiments reported, the most effective time course was reported to be weekly injections for 4 weeks. (E.g., U.S. Pat. No. 5,488,036, col. 20, lines 46–47.) Because most of the conjugates cited are relatively large compounds, antigenicity could be a problem when such multiple administrations are used. The GnRH analog was preferably linked to the toxin with one of several specified heterobifunctional reagents. The specifications suggest that considerable effort was expended in conjugating the toxin to the GnRH agonist. The toxins must in general be internalized into the target cells to have effect, and do not act on cell membranes; in addition, at least some of these toxins must be secondarily transported from the membrane-bound vesicle into the cytoplasm to interact with ribosomes, mitochondria, or other cellular components.

DISCLOSURE OF INVENTION

It has been unexpectedly discovered that amphipathic lytic peptides are ideally suited to use in a ligand/cytotoxin combination to specifically induce sterility or long-term contraception in mammals. The peptides act directly on cell membranes, and need not be internalized. Administering a combination of gonadotropin-releasing hormone (GnRH) (or a GnRH agonist) and a membrane-active lytic peptide produces long-term contraception or sterilization in mammals in vivo. Particularly surprising, sterility results even when the combination is administered to a sexually immature animal: The combination then prevents sexual maturation.

The compounds used in the present invention are relatively small, and will not be antigenic. (Lytic peptides are known not to be very antigenic; and the ligands are not antigenic at all.) The compounds may be administered in a single dose, although they may also be given in two or more closely spaced doses. Lysis of gonadotropes has been observed to be very rapid (on the order of ten minutes.) The two components—the ligand and the lytic peptide—may optionally be administered as a fusion peptide, or they may be administered separately, with the ligand administered slightly before the lytic peptide, to activate cells with receptors for the ligand, and thereby make those cells susceptible to lysis by the lytic peptide. If a fusion peptide is used, it has been unexpectedly discovered that a linking moiety is not necessary to join the ligand to the lytic peptide: one may be bonded directly to the other, without the need for any intervening linkage; bonding is preferably performed by bonding one end of the ligand to one end of the peptide, not by bonding to the middle of either. The toxin; the lytic peptide, does not need a translocation domain, and need not be internalized, as it binds to and acts directly on the activated cell membrane to cause lysis.

MODES FOR CARRYING OUT THE INVENTION

It is known that the D-amino acid form of GnRH will bind to gonadotropes in the pituitary and to GnRH neurons in the brain. It is also known that the D-amino acid forms of lytic peptides have essentially the same propensity to lyse cell membranes as do the L-amino acid forms. Compounds of the present invention (whether administered as a fusion peptide or separately) may therefore be administered either in L-form or D-form. D-form peptides, although generally more expensive than L-form, have the advantage that they are not degraded by normal enzymatic processes, so that the D-form peptides may therefore be administered orally and generally have a longer, biological half-life. Oral administration of the D-form peptide may be enhanced by linking the peptide/hormone fusion product to a suitable carrier to facilitate uptake by the intestine, for example vitamin $B_{12}$, following generally the $B_{12}$-conjugation technique of G. Russell-Jones et al., "Synthesis of LHRH Antagonists Suitable for Oral Administration via the Vitamin $B_{12}$ Uptake System," *Bioconjugate Chem.*, vol. 6, pp. 34–42 (1995).

GnRH or GnRH analogs (collectively, "GnRH agonists") may be used in the present invention. It has been reported that substitutions at the 6 and 10 positions of the GnRH decapeptide can produce "superagonists" having greater binding affinity to the GnRH receptor than does GnRH itself. These "superagonists" include goserelin, leuprolide, buserelin, and nafarelin. See U.S. Pat. No. 5,488,036.

Without wishing to be bound by this theory, it is believed that the mechanism underlying the invention is as follows: GnRH activates gonadotropic cells in the pituitary gland, as well as neuroendocrine GnRH neurons in the brain. The activated cells have substantially increased susceptibility to lysis by a lytic peptide. The lytic peptide then preferentially destroys (or severely damages) these activated cells. When the gonadotrophic cells in the pituitary are destroyed and are deprived of GnRH from the brain, the pituitary no longer secretes follicle stimulating hormone (FSH) or luteinizing hormone (LH), rendering the mammal temporarily or permanently sterile.

Although the ligand and the lytic peptide may be administered separately, it is preferred to link the two in a single molecule, because such a linkage greatly increases the effective concentration of the lytic peptide in the vicinity of ligand-activated cells. Furthermore, this increase in the effective lytic peptide concentration can obviate the need for activation of the cells, allowing the peptide to be linked to a binding site of a ligand alone, without needing to include the "remainder" of a native ligand that would normally be needed for activating the target cells. This linkage may be in either order: for example, GnRH/peptide or peptide/GnRH. Examples are GnRH/hecate (SEQ. ID NO. 3) and hecate/GnRH (SEQ. ID NO. 4). Note that no intermediate linker is necessary, and that the carboxy terminus of one of the two peptides may be bonded directly to the amino terminus of the other. (We have found that the initial pyro-glutamic acid residue of the GnRH or the GnRH portion of a fusion peptide may be substituted with glutamine without substantially changing the activity of the respective peptides. See, e.g., SEQ. ID Nos. 9, 3, and 4.)

EXPERIMENTAL RESULTS

EXAMPLES 1–6

The pituitary gland of an adult female rat was harvested and divided into six sections of approximately equal size. One section was placed in each of six wells containing tissue culture medium at 37° C. A different treatment was applied to each well, as described below. Ten hours after treatment, the tissue from each well was fixed, and the histology of each was examined microscopically.

Treatment 1 applied tissue culture medium alone as a control. The histology of this tissue after treatment appeared normal.

Treatment 2 was an application of 5 nanograms of GnRH (SEQ. ID NO. 1) per mL of medium. The histology of this tissue after treatment was normal; a small degree of cellular vacuolization was noted. For comparison, the concentration of GnRH in normal, untreated rats varies from as low as 1 ng/mL to as high as 20 ng/mL during the LH surge phase of the estrous cycle.

Treatment 3 was an application of 50 μM of the lytic peptide hecate (SEQ. ID NO. 2) in the medium. The histology of this tissue after treatment appeared normal.

Treatment 4 was an initial application of 5 nanograms of GnRH per mL of medium for 15 minutes. Following this incubation, the medium containing GnRH was removed, and the tissue was washed once with plain medium. This medium was then removed, and was replaced with medium containing 50 μM of the lytic peptide hecate. Widespread basophilic (gonadotropic) cellular destruction was observed after this treatment.

Treatment 5 was an application of 50 μM of the fusion peptide modified GnRH/hecate (SEQ. ID NO. 3). Widespread basophilic (gonadotropic) cellular destruction was observed after the treatment.

Treatment 6 was an initial application of the fusion peptide GnRH/hecate (SEQ. ID NO. 3), followed by a second application of the fusion peptide GnRH/hecate two hours later. After treatment the tissue was virtually destroyed, with only stromal cells remaining.

EXAMPLE 7

Two sexually immature female rats from the same litter (age 33 days) were given two intravenous injections of saline control solution 24 hours apart. After the rats reached breeding age, they were examined 105 days post-inoculation. The external genitalia appeared normal. During a fourteen-day monitoring period 107 days to 121 days post-inoculation, each of the control rats completed two estrous cycles. The rats were then sacrificed and necropsied. The reproductive organs appeared histologically normal.

EXAMPLE 8

Two sexually immature female rats from the same litter as those of Example 7 (age 33 days) were given two intravenous injections of 500 μg GnRH/hecate fusion peptide in saline 24 hours apart. After the rats reached breeding age, they were examined 105 days post-inoculation. The external genitalia appeared small. Unlike the control rats, insertion of a cotton-tipped swab into the vagina was difficult. During a fourteen-day monitoring period 107 days to 121 days post-inoculation, neither of the treated rats demonstrated estrous or metestrous. The rats were then sacrificed and necropsied. The peptide-treated rats had thinned, inactive uterine and oviductal epithelia. Their ovaries contained no large follicles, and had a high number of atretic follicles (i.e., those that had failed to ovulate).

EXAMPLES 9–14

Eighteen sexually mature, mixed breed, female rats were randomly assigned to one of six groups containing three rats each. Each group of rats received a double treatment intravenously, as described below. Two weeks after the treatment, the rats were sacrificed and necropsied. The reproductive and endocrine organs were sectioned, weighed, and examined histologically.

Treatment 9 was a saline control. The rats in this group exhibited normal ovarian function (e.g., normal follicles and new corpora lutea). The pituitaries from this group were of normal size. Histology showed a normal number of pituitary basophilic cells.

Treatment 10 was injection with a total of 1.0 mg GnRH/hecate fusion peptide in saline, divided into two equal 0.5 mg injections administered 24 hours apart. The rats in this group showed an arrest of normal ovarian follicular development. Few corpora lutea were present, and those that were present appeared old. Follicles were large, and had not ruptured. Uterine morphology was consistent with hormonal inactivity. The pituitaries from this group were slightly smaller than the pituitaries from the saline control group. Histology revealed a 60% to 70% reduction in the number of pituitary basophilic cells compared to the controls.

Treatment 11 was injection of 100 μL of a 1.35 mM solution of GnRH (162 μg) in saline, followed 15 minutes later by injection with 100 μL of a 1.35 mM solution of hecate (337 μg) in saline. The same two-step treatment was repeated 24 hours later. The rats in this group showed altered ovarian histology. Few corpora lutea were present, and those that were present appeared old. Follicles were large, and had not ruptured. Uterine morphology was consistent with hormonal inactivity. The pituitaries and the pituitary histology were similar to those observed in Treatment 10.

Treatment 12 was injection of 100 μL of a 1.35 mM solution of hecate (337 μg) in saline. The treatment was repeated after 24 hours. The rats in this group exhibited normal ovarian function (e.g., normal follicles and new corpora lutea). The pituitaries and the pituitary histology were similar to those observed in Treatment 9.

Treatment 13 was injection of 100 μL of a 1.35 mM solution of GnRH (162 μg) in saline. The treatment was repeated after 24 hours. The rats in this group exhibited normal ovarian function (e.g., normal follicles and new corpora lutea). The pituitaries and the pituitary histology were similar to those observed in Treatment 9.

Treatment 14 was identical to Treatment 10, except that the GnRH/hecate fusion peptide was further purified by HPLC. The rats in this group showed an arrest of normal ovarian follicular development. Few corpora lutea were present, and those that were present appeared old. Follicles were large, and had not ruptured. Uterine morphology was consistent with hormonal inactivity. The pituitaries and the pituitary histology were similar to those observed in Treatment 10.

These experiments demonstrate that GnRH and the lytic peptide may be administered either separately or as a fusion peptide, although the fusion peptide is preferred as it is expected to be more active at lower doses.

Although experiments to determine optimum dosages had not been performed by the time this application is being filed, a person of ordinary skill in the art, who is given the teachings of the present specification, may readily ascertain optimum dosages through routine testing.

Although the experiments to date have been performed on female mammals, similar results are expected for male mammals, because GnRH signals pituitary cells to release gonadotropins in both males and females.

Tissue and cell specificity of cytotoxic conjugates could be further enhanced by using various hormones or hormone analogs coupled to a lytic peptide. Some examples follow. For fertility control, both the pituitary and the central GnRH neuronal component of the reproductive axis are selectively damaged by GnRH-hecate conjugate. Few cells in the central nervous system should be damaged by this treatment, because the chicken II GnRH and lamprey III GnRH forms are the primary molecules affecting brain function in most mammals. Fertility control may also be selectively accomplished by treating animals with a bLH-hecate conjugate; this compound should specifically affect GnRH neurons controlling reproduction and the gonads. (Other lytic peptides may be used in place of hecate in these conjugates.)

The compositions of the present invention may be administered as described, or as pharmaceutically acceptable salts. The compositions may be administered intravenously, subcutaneously, intramuscularly, cr (especially when in D-amino acid form and complexed with a carrier such as vitamin $B_{12}$) orally.

Applications of the present invention include long-term contraception or sterilization in humans; and long-term contraception or sterilization in domesticated or wild mammals. Domesticated mammals in which this invention may be used include, for example, dogs, cats, cattle, horses, pigs, and sheep. When used in humans, long-term replacement hormone therapy may be needed to prevent undesirable side effects, such as premature menopause. Administration of gonadotropic hormones in a sterilized individual will temporarily restore fertility if desired. The sterilization is reversible in this sense.

As one example, this invention may be used in the humane population control of an unwanted introduced species.

EXAMPLES 15–22

Eight sexually mature, Sprague-Dawley female rats were randomly assigned to one of eight treatments. Each group of rats received a single treatment intravenously, as described below. Rats were sacrificed and necropsied either 48 or 96 hours after treatment. The ovaries, uterus, pancreas, liver, spleen, lungs, heart, thyroid, and adrenal glands were fixed in 10% buffered formalin; sectioned; and stained with H&E (hematoxylin and eosin) stain; except that the pituitary glands were stained with PAS (periodic acid-Schiff) stain with no counter-stain. The treatments were selected so that each animal received an equimolar amount of the compound with which it was treated.

Treatments 15 and 16 were IV-injection with 674 µg of D-hecate in 200 µL saline (1.35 mM). The rat in treatment 15 was sacrificed 48 hours after injection, and the rat in treatment 16 was sacrificed 96 hours after injection. No gross lesions were noted in the organs of either animal. The pituitary glands of both rats contained a normal number of PAS-positive cells.

Treatments 17 and 18 were IV-injection with 334 µg of GnRH in 200 µL saline (1.35 mM). The rat in treatment 17 was sacrificed 48 hours after injection, and the rat in treatment 18 was sacrificed 96 hours after injection. No gross lesions were noted in the organs of either animal. The pituitary glands of both rats contained a normal number of PAS-positive cells.

Treatments 19–22 were IV-injection with 1 mg GnRH-hecate fusion peptide (SEQ. ID NO. 3) in 100 µL saline (2.7 mM). The rats in treatments 19 and 20 were sacrificed 48 hours after injection, and the rats in treatments 21 and 22 were sacrificed 96 hours after injection. No gross lesions were noted in the organs of any of the four animals, other than the pituitary. The pituitary glands of the animals from treatments 19 and 20 were slightly enlarged, hyperemic, and edematous. The pituitary glands of the animals from treatments 21 and 22 were slightly hyperemic, but of expected size. The pituitary glands of all four rats showed a marked depletion of PAS-positive cells; it was estimated that the depletion was 80 to 90% compared to those of control groups. (PAS stain preferentially stains glycopeptides. LH, FSH, and MSH are glycopeptide hormones; cells containing these hormones stored in their secretory vacuoles stain positive with PAS.)

It was thus seen that the GnRH-lytic peptide combination caused morphological and functional alterations in the adult female rat reproductive system, and in preventing sexual maturity in pre-pubertal female rats, but that the fusion peptide selectively eliminated a specific population of PAS-positive staining cells in the pituitary.

EXAMPLE 23

Subsequent experiments were conducted on rats using treatments generally similar to treatments 9–14 above. Observations made with immunohistochemical staining found that the effective treatments selectively killed (1) gonadotropes in the pituitary, and (2) neurons in the brain bearing GnRH receptors. The selective killing of these cells was seen after the GnRH-hecate fusion peptide was administered; and after the administration of GnRH alone, followed 10 minutes later by the administration of hecate alone. In these cases, it was also observed that pituitary cells no longer secreted either LH or FSH following the effective treatments.

EXAMPLE 24

Hecate is an amphipathic lytic peptide that acts on cell membranes without being internalized. It is a synthetic peptide analog of melittin, the primary toxin in honeybee venom. Hecate is believed to act by disrupting cell membranes. The structure of the modified GnRH-hecate conjugate used in these studies was SEQ. ID NO. 3.

We also synthesized D-Lys$^6$GnRH (SEQ. ID NO. 13), so that hecate could be conjugated to the D-Lys$^6$, a position that could minimize interference with binding of the GnRH domain to the GnRH receptor. These synthetic peptides specifically displaced radiolabelled monoiodinated-GnRH from rat pituitary membranes. Displacement by D-Lys$^6$GnRH-hecate was comparable to (and actually slightly greater than) displacement by native mammalian GnRH, as measured by cpm of radioactivity. When GnRH and GnRH-hecate binding were compared on a molar basis over a 1000-fold concentration range (n=6) the GnRH-hecate specifically displaced the radiolabelled peptide to an extent equal to 123%±4% of the binding exhibited by equimolar concentrations of GnRH; equimolar concentrations of D-Lys$^6$GnRH displaced 187%±8% of the cpm displaced by native GnRH.

EXAMPLES 25–32

We studied in vitro lysis of bovine luteal cells with GnRH-hecate conjugate and with hecate-bLH conjugate (SEQ. ID NO. 12). (The bLH component of the conjugate is a 15-mer fragment of the beta chain of luteinizing hormone, SEQ. ID NO. 11). Small luteal cells were collected from cattle corpora lutea post-slaughter. Small luteal cells are rich in LH receptors, and were found to be highly susceptible to lysis by the hecate-bLH conjugate.

Small luteal cells in culture were incubated with one of the following treatments for 22 hours, and were then examined for viability using Trypan Blue exclusion and release of lactic dehydrogenase.

Treatment 25 control: no additional treatment (media alone)

Treatment 26 10 ng bLH (positive control)

Treatment 27 hecate-bLH, 10 µM

Treatment 28 hecate-bLH, 5 µM

Treatment 29 hecate-bLH, 1 µM

Treatment 30 hecate (alone), 10 µM

Treatment 31 hecate (alone), 5 µM

Treatment 32 hecate (alone), 1 µM

Significant killing of small luteal cells was observed following 22 hr. incubation with 10 µM hecate alone, and with 5 µM hecate alone (approximately 50% killing). Cell death for 1 µM hecate alone did not differ significantly from negative control (media) or from bLH alone. All three treatment doses with hecate-bLH caused significant increases in cell death as compared to treatment with hecate alone. The hecate-bLH conjugate killed approximately twice the number of cells as were killed by hecate alone at the same concentrations.

Observed levels of lactic dehydrogenase activity also demonstrated that the hecate-bLH treatment killed a significantly greater number of cells than did hecate alone.

EXAMPLES 33–34

We also studied in vitro lysis of bovine granulosa cells with GnRH-hecate conjugate and with hecate-bLH conjugate. Granulosa cells were isolated from bovine preovulatory follicles. (Granulosa cells are hormonally active cells with numerous LH receptors.) Our experiments with granulosa cells were otherwise generally similar to those described above for Examples 25–32. These experiments demonstrated (1) that the granulosa cells were much more susceptible to killing by hecate alone than were the small luteal cells, and (2) that, as had been the case with the small luteal cells, the granulosa cells were significantly more susceptible to hecate-bLH at even the lowest concentration (1 $\mu$M) than they were to hecate alone. At 1 $\mu$M, the hecate-bLH conjugate killed about twice the number of target cells as did hecate alone. Again, the levels of lactic dehydrogenase released following the hecate-bLH 1 $\mu$M treatment were significantly higher than the levels of enzyme released following treatment with 1 $\mu$M hecate alone.

Additional studies (data not shown) demonstrated that a 15-mer fragment of the bLH subunit specifically bound to LH receptors on the target granulosa cells, but did not initiate the production of steroid hormones that would be indicative of a stimulus-coupled response. We thus demonstrated that the selective killing of target cells resulted from the physical proximity of the lytic peptide to the cell, which was caused by binding of the LH subunit. Stimulation of target cell hormone production was not required for cell lysis. This result was surprising, as we had previously expected that activation of the target cells was required for increased susceptibility to lysis. These data demonstrate that such activation is not required. These data are, however, consistent with our other data showing that cell activation is also a route that can lead to increased susceptibility to the lytic peptide.

EXAMPLES 35–38

Another set of experiments was performed to study the in vivo effects of the GnRH-hecate conjugate on female rats and rabbits. The ovaries, uterus, oviducts, adrenals, spleen, thyroids, pancreas, liver, lungs, and heart were processed for histological analysis. The pituitaries were processed for histological analysis of PAS-stained cells and for cells stained immunocytochemically for bLH, BFSH (bovine follicle stimulating hormone), adrenocorticotropic hormone, and other proopiomelanocortin peptide products (most notably alpha-melanocyte stimulating hormone (MSH)), thyroid stimulating hormone (TSH), prolactin (PRL), vasopressin (VP), oxytocin (OXY) or growth hormone (GH). The immunocytochemical staining procedures we used followed generally the procedures of M. Rahmanian et al., "Histological and immunocytochemical characterization of pituitary cell types in ponies," *Proc. 13th Soc. Equine Nutrition & Phys. Symp.*, pp. 348–349 (1993); M. Rahmanian et al., "Immunocytochemical localization of luteinizing hormone and follicle-stimulating hormone in the equine pituitary," *J. Anim. Sci.*, vol. 76, pp. 839–846 (1998); M. Rahmanian et al., "Immunocytochemical localization of prolactin and growth hormone in the equine pituitary," *Animal Sci.*, vol. 75, pp. 3010–3018 (1997); and P. Melrose et al., "Comparative topography of the immunoreactive alpha-melanocyte-stimulating hormone neuronal system in the brains of horses and rats," *Brain Beh. & Evol.*, vol. 32, pp. 226–235 (1988).

Brains were serially sectioned on a Vibrotome from the level of the diagonal band of Broca to the mammillary body. Alternate sections were consecutively divided into four to five dishes, and sections in alternate dishes were stained with cresyl violet, or were stained immunocytochemically for GnRH or the GnRH precursor, VP, OXY, or tyrosine hydroxylase (the rate-limiting enzyme in catecholamine synthesis). In addition to the staining procedures cited above, we also used the immunocytochemical staining procedures of P. Melrose et al., "Distribution and morphology of immunoreactive gonadotropin-releasing hormone (GnRH) neurons in the basal forebrain of ponies," *J. Comp. Neurol.* vol. 339, pp. 269–287 (1994); and P. Melrose et al., "Topography of oxytocin and vasopressin neurons in the forebrain of Equus caballus: Further support of proposed evolutionary relationships for proopiomelanocortin, oxytocin and vasopressin neurons," *Brain, Beh. & Evol.*, vol. 33, pp. 193–204 (1989).

Thirty-three-day-old, sexually immature female rats were given intravenous administrations as follow:

Treatment 35: 0.03 $\mu$g GnRH (a normal physiological dose) (two rats)

Treatment 36: 1.62 $\mu$g GnRH (the molar equivalent to the amount of GnRH in Treatment 37) (one rat)

Treatment 37: 0.5 mg GnRH-hecate (one rat)

Treatment 38: 0.03 $\mu$g GnRH, followed 11 minutes later by 0.337 $\mu$g hecate (two rats).

Animals were sacrificed 14 days after treatment. As compared to the two GnRH control groups, the treatment with GnRH-hecate and the treatment with GnRH followed by hecate alone reduced pituitary weights by 13% and 14%, respectively, and reduced the numbers of bLH-specific gonadotropes by 92% and 87%, respectively. Further, following these two experimental treatments the cell bodies of GnRH-stained neurons in hypophysiotropic areas of the brain were frequently deformed; and a substantial amount of immunoreactive material leached into surrounding areas where numerous cell bodies are concentrated (the organum vasculosum of the lamina terminalis). There was histological damage to cells from the two experimental treatments in the C1 and C3 fields of the hippocampus, and increased staining of parvicellular VP neurons in the paraventricular nucleus. (The VP staining may have been caused by formation of a precipitate in certain areas of the brain. Subsequent studies with more highly purified peptide did not show a precipitate). The change in VP expression, probably in corticotropin-releasing neurons, may cause a shift in the post-translational processing of proopiomelanocortin peptide products in the pars distalis, since GnRH-hecate and GnRH+hecate treatments reduced adrenocorticotropic hormone levels and increased the number of alpha-MSH-stained cells in this subdivision of the pituitary. No pathological changes were noted in any other tissues.

Since neurons in the brain do not regenerate, severe damage to these neurons could make sterilization with a GnRH/lytic peptide combination permanent (but temporarily reversible by administration of gonadotrophic hormones).

EXAMPLES 39–43

Sexually immature (33 day old) female rats (randomly allocated into groups of three) were injected intravenously with saline or GnRH-hecate in saline as follows:

Treatment 39: 0.0 mg GnRH-hecate

Treatment 40: 0.1 mg GnRH-hecate

Treatment 41: 0.5 mg GnRH-hecate

Treatment 42: 1.0 mg GnRH-hecate

Treatment 43: 1.5 mg GnRH-hecate.

Animals were sacrificed at 24 hours or at 14 days after treatment. Results were similar to those reported above for Examples 35–38, except that no precipitate was found in the brain, and VP staining in the CNS was not altered. The treatments with higher levels of GnRH-hecate produced a large number of GnRH-receptor-containing neurons having abnormal morphologies, including distortion of the somatic portion of the cells, and degeneration of neurites. In the rats sacrificed fourteen days after treatment, 66% and 87% of the GnRH-receptor-containing neurons were abnormal in the rats that had received 1.0 and 1.5 mg of GnRH-hecate, respectively. Axonal degeneration in the 1.5 mg GnRH-hecate group was accompanied by over 90% reduction in median eminence staining for GnRH.

EXAMPLES 44–46

Seven sexually mature female New Zealand rabbits were injected intravenously with saline containing GnRH-hecate as follows:

Treatment 44: 0 mg GnRH-hecate (n=3)

Treatment 45: 5 mg GnRH-hecate (n=3)

Treatment 46: 10 mg GnRH-hecate (n=1).

Forty-six days later all rabbits were injected intramuscularly with 100 µg GnRH. Blood samples were collected at 0, 1, 4, and 24 hours, and LH and FSH levels in the blood samples were measured by radioimmunoassay. Hormone analyses revealed that both control and experimental animals released LH in response to the GnRH, suggesting that there may be at least some degree of reversibility following treatment, at least for pituitary gonadotropes at lower doses of ligand/peptide. The rabbits were sacrificed the next day (day 47) for postmortem histological analysis. We found that the numbers of tertiary follicles, corpora lutea, and GnRH-induced ovulations were reduced by GnRH-hecate treatment. Ovarian and pituitary weights were reduced by the 10 mg GnRH-hecate treatment. In tissues from the GnRH-hecate treatments, observed immunoreactive GnRH was faint and diffusely localized in CNS areas normally containing cell bodies; normal individual cell bodies were reduced in number by at least 50%; and the terminal fields, which normally contain the axons of GnRH receptor neurons, were not stained for GnRH. These observations suggest that the most pronounced effects of the GnRH-hecate treatments in these experiments on rabbits may have been on neuroendocrine neurons in the brain. The hippocampus and other areas of the brain containing high concentrations of GnRH were not discernibly affected by GnRH-hecate treatments. The GnRH-hecate treatment increased the number of PAS-stained pituitary cells in the pars distalis to 177% of that for control rabbits; this increase appeared to reflect increased numbers of cells staining alpha-MSH, and reduced numbers of cells staining for LH.

EXAMPLES 47–48

Nine sexually mature female rabbits were injected intravenously with saline containing 0 mg (n=4) (Treatment 47) or 10 mg GnRH-hecate (n=5) (Treatment 48). Rabbits were injected intramuscularly with GnRH on day 6 post-treatment. Blood samples were collected for radioimmunoassay of LH and FSH as described above, and the animals were sacrificed on day 7 post-treatment. Both control and experimental animals released LH in response to the GnRH; however, the amount of LH released was lower in the treated animals than in the controls. The GnRH-hecate treatment reduced the numbers of tertiary ovarian follicles, and the numbers of GnRH-induced ovulations. No effects were noticed either on peripheral tissues or on pituitary weight. The effects of GnRH-hecate on CNS morphology and immunocytochemical results were similar to those described above in Examples 35–46. Again, the effects were more pronounced on GnRH neurons than on staining of pituitary gonadotropes.

The number of ovulation sites in rabbits in Examples 47 and 48 treated with 10 mg GnRH-hecate were reduced as compared to saline controls. The mean number of ovulation sites in four saline controls equalled 12.2±5.4, with S.E.M.=2.7. The mean number of ovulation sites in the five rabbits given 10 mg of GnRH-hecate was 3.6±1.1, with S.E.M.=0.5. This difference from control was significant (p=0.025).

The "LH surge" (the level of LH at one hour post-GnRH challenge, minus the resting level before challenge) in the four controls was 61.2±16.5 ng/mL, with S.E.M.=8.3; and in the treated group was 49.6±26.1 ng/mL, with S.E.M.=12 (p=0.22). Thus there was a trend towards lower LH levels in the treated group.

The in vivo studies clearly demonstrated that the GnRH-hecate conjugate selectively damaged GnRH receptor-bearing cells in the brain (neurons) and in the pituitary (gonadotrophic cells). Further, these studies demonstrated a significant alteration in the ovary, presumably a consequence of alteration in the reproductive centers of the brain-pituitary axis. Selectivity of the conjugate was demonstrated by the following observations: (1) No cytotoxic changes were seen in neurons that lacked GnRH receptors. (2) No changes were seen in pituitary cells that lacked GnRH receptors. (3) No changes were seen in other endocrine and non-endocrine tissues (except for the ovary, which presumably responded indirectly to the destruction of gonadotrophs in the pituitary).

Many of the events referred to as "ovulations" in the GnRH-hecate treated rabbits possibly were not functional ovulation sites, but may instead have represented hemorrhagic pre-ovulatory degenerative changes. Additional breeding trials will be conducted to verify that ovulation of functional ova is prevented.

Lytic Peptides Useful in the Present Invention

It is believed (without wishing to be bound by this theory) that lytic peptides act by disrupting cell membranes. "Resting" eukaryotic cells protect themselves through their ability to repair the resulting membrane damage. By contrast, activated cells (e.g., cells stimulated by GnRH) are unable (or less able) to repair damaged membranes. Because GnRH-activated pituitary cells have a diminished capacity to repair membranes, they are preferentially destroyed by lytic peptides, while adjacent non-activated cells repair their membranes and survive.

Although the embodiments of this invention that have been tested to date have used hecate as the effector lytic peptide, this invention will work with a combination of GnRH with other lytic peptides as well. Many lytic peptides are known in the art and include, for example, those mentioned in the references cited in the following discussion.

Lytic peptides are small, basic peptides. Native lytic peptides appear to be major components of the antimicrobial defense systems of a number of animal species, including those of insects, amphibians, and mammals. They typically comprise 23–39 amino acids, although they can be smaller. They have the potential for forming amphipathic alpha-helices. See Boman et al., "Humoral immunity in *Cecropia* pupae," *Curr. Top. Microbiol. Immunol.* vol. 94/95, pp. 75–91 (1981); Boman et al., "Cell-free immunity in insects," *Annu. Rev. Microbiol.*, vol. 41, pp. 103–126 (1987); Zasloff, "Magainins, a class of antimicrobial peptides from Xenopus skin: isolation, characterization of two active forms, and partial DNA sequence of a precursor," *Proc. Natl. Acad. Sci. USA*, vol. 84, pp. 3628–3632 (1987); Ganz et al., "Defensins natural peptide antibiotics of human neutrophils," *J. Clin. Invest.*, vol. 76, pp. 1427–1435 (1985); and Lee et al., "Antibacterial peptides from pig intestine: isolation of a mammalian cecropin," *Proc. Natl. Acad. Sci. USA*, vol. 86, pp. 9159–9162 (1989).

Known amino acid sequences for lytic peptides may be modified to create new peptides that would also be expected to have lytic activity by substitutions of amino acid residues that preserve the amphipathic nature of the peptides (e.g., replacing a polar residue with another polar residue, or a non-polar residue with another non-polar residue, etc.); by substitutions that preserve the charge distribution (e.g., replacing an acidic residue with another acidic residue, or a basic residue with another basic residue, etc.); or by lengthening or shortening the amino acid sequence while preserving its amphipathic character or its charge distribution. Lytic peptides and their sequences are disclosed in Yamada et al., "Production of recombinant sarcotoxin IA in *Bombyx mori* cells," *Biochem. J.*, vol. 272, pp. 633–666 (1990); Taniai et al., "Isolation and nucleotide sequence of cecropin B cDNA clones from the silkworm, *Bombyx mori*," *Biochimica Et Biophysica Acta*, vol. 1132, pp. 203–206 (1992); Boman et al., "Antibacterial and antimalarial properties of peptides that are cecropin-melittin hybrids," *Febs Letters*, vol. 259, pp. 103–106 (1989); Tessier et al., "Enhanced secretion from insect cells of a foreign protein fused to the honeybee melittin signal peptide," *Gene*, vol. 98, pp. 177–183 (1991); Blondelle et al., "Hemolytic and antimicrobial activities of the twenty-four individual omission analogs of melittin," *Biochemistry*, vol. 30, pp. 4671–4678 (1991); Andreu et al., "Shortened cecropin A-melittin hybrids. Significant size reduction retains potent antibiotic activity," *Febs Letters*, vol. 296, pp. 190–194 (1992); Macias et al., "Bactericidal activity of magainin 2: use of lipopolysaccharide mutants," *Can. J. Microbiol.*, vol. 36, pp. 582–584 (1990); Rana et al., "Interactions between magainin-2 and *Salmonella typhimurium* outer membranes: effect of Lipopolysaccharide structure," *Biochemistry*, vol. 30, pp. 5858–5866 (1991); Diamond et al., "Airway epithelial cells are the site of expression of a mammalian antimicrobial peptide gene," *Proc. Natl. Acad. Sci. USA*, vol. 90, pp. 4596 ff (1993); Selsted et al., "Purification, primary structures and antibacterial activities of β-defensins, a new family of antimicrobial peptides from bovine neutrophils," *J. Biol. Chem.*, vol. 268, pp. 6641 ff (1993); Tang et al., "Characterization of the disulfide motif in BNBD-12, an antimicrobial β-defensin peptide from bovine neutrophils," *J. Biol. Chem.*, vol. 268, pp. 6649 ff (1993); Lehrer et al., *Blood*, vol. 76, pp. 2169–2181 (1990); Ganz et al., *Sem. Resp. Infect. I.*, pp. 107–117 (1986); Kagan et al., *Proc. Natl. Acad. Sci. USA*, vol. 87, pp. 210–214 (1990); Wade et al., *Proc. Natl. Acad. Sci. USA*, vol. 87, pp. 4761–4765 (1990); Romeo et al., *J. Biol. Chem.*, vol. 263, pp. 9573–9575 (1988); Jaynes et al., "Therapeutic Antimicrobial Polypeptides, Their Use and Methods for Preparation," WO 89/00199 (1989); Jaynes, "Lytic Peptides, Use for Growth, Infection and Cancer," WO 90/12866 (1990); Berkowitz, "Prophylaxis and Treatment of Adverse Oral Conditions with Biologically Active Peptides," WO 93/01723 (1993).

Families of naturally-occurring lytic peptides include the cecropins, the defensins, the sarcotoxins, the melittins, and the magainins. Boman and coworkers in Sweden performed the original work on the humoral defense system of *Hyalophora cecropia*, the giant silk moth, to protect itself from bacterial infection. See Hultmark et al., "Insect immunity. Purification of three inducible bactericidal proteins from hemolymph of immunized pupae of *Hyalophora cecropia*," *Eur. J. Biochem.*, vol. 106, pp. 7–16 (1980); and Hultmark et al., "Insect immunity. Isolation and structure of cecropin D. and four minor antibacterial components from *cecropia* pupae," *Eur. J. Biochem.*, vol. 127, pp. 207–217 (1982).

Infection in *H. cecropia* induces the synthesis of specialized proteins capable of disrupting bacterial cell membranes, resulting in lysis and cell death. Among these specialized proteins are those known collectively as cecropins. The principal cecropins—cecropin A, cecropin B, and cecropin D—are small, highly homologous, basic peptides. In collaboration with Merrifield, Boman's group showed that the amino-terminal half of the various cecropins contains a sequence that will form an amphipathic alpha-helix. Andrequ et al., "N-terminal analogues of cecropin A: synthesis, antibacterial activity, and conformational properties," *Biochem.*, vol. 24, pp. 1683–1688 (1985). The carboxy-terminal half of the peptide comprises a hydrophobic tail. See also Boman et al., "Cell-free immunity in Cecropia," *Eur. J. Biochem.*, vol. 201, pp. 23–31 (1991).

A cecropin-like peptide has been isolated from porcine intestine. Lee et al., "Antibacterial peptides from pig intestine: isolation of a mammalian cecropin," *Proc. Natl. Acad. Sci. USA*, vol. 86, pp. 9159–9162 (1989).

Cecropin peptides have been observed to kill a number of animal pathogens other than bacteria. See Jaynes et al., "In Vitro Cytocidal Effect of Novel Lytic Peptides on *Plasmodium falciparum* and *Trypanosoma cruzi*," FASEB, 2878–2883 (1988); Arrowood et al., "Hemolytic properties of lytic peptides active against the sporozoites of *Cryptosporidium parvum*," *J. Protozool.*, vol. 38, No. 6, pp. 161S–163S (1991); and Arrowood et al., "In vitro activities of lytic peptides against the sporozoites of *Cryptosporidium parvum*," *Antimicrob. Agents Chemother.*, vol. 35, pp. 224–227 (1991). However, normal mammalian cells do not appear to be adversely affected by cecropins, even at high concentrations. See Jaynes et al., "In vitro effect of lytic peptides on normal and transformed mammalian cell lines," *Peptide Research*, vol. 2, No. 2, pp. 1–5 (1989); and Reed et al., "Enhanced in vitro growth of murine fibroblast cells and preimplantation embryos cultured in medium supplemented with an amphipathic peptide," *Mol. Reprod. Devel.*, vol. 31, No. 2, pp. 106–113 (1992).

Defensins, originally found in mammals, are small peptides containing six to eight cysteine residues. Ganz et al., "Defensins natural peptide antibiotics of human neutrophils," *J. Clin. Invest.*, vol. 76, pp. 1427–1435 (1985). Extracts from normal human neutrophils contain three defensin peptides: human neutrophil peptides HNP-1, HNP-2, and HNP-3. Defensin peptides have also been described in insects and higher plants. Dimarcq et al., "Insect immunity: expression of the two major inducible antibacterial peptides, defensin and diptericin, in *Phormia terranvae*," *EMBO J.*, vol. 9, pp. 2507–2515 (1990); Fisher et al., *Proc. Natl. Acad. Sci. USA*, vol. 84, pp. 3628–3632 (1987).

Slightly larger peptides called sarcotoxins have been purified from the fleshfly *Sarcophaga peregrina*. Okada et al., "Primary structure of sarcotoxin I, an antibacterial protein induced in the hemolymph of *Sarcophaga peregrina* (flesh fly) larvae," *J. Biol. Chem.*, vol. 260, pp. 7174–7177 (1985). Although highly divergent from the cecropins and defensins, the sarcotoxins presumably have a similar antibiotic function.

Other lytic peptides have been found in amphibians. Gibson and collaborators isolated two peptides from the African clawed frog, *Xenopus laevis*, peptides which they named PGS and Gly$^{10}$Lys$^{22}$PGS. Gibson et al., "Novel peptide fragments originating from PGL$_a$ and the caervlein and xenopsin precursors from *Xenopus laevis*," *J. Biol. Chem.*, vol. 261, pp. 5341–5349 (1986); and Givannini et al., "Biosynthesis and degradation of peptides derived from *Xenopus laevis* prohormones," *Biochem. J.*, vol. 243, pp. 113–120 (1987). Zasloff showed that the Xenopus-derived peptides have antimicrobial activity, and renamed them magainins. Zasloff, "Magainins, a class of antimicrobial peptides from Xenopus skin: isolation, characterization of two active forms, and partial DNA sequence of a precursor," *Proc. Natl. Acad. Sci. USA*, vol. 84, pp. 3628–3632 (1987).

Synthesis of nonhomologous analogs of different classes of lytic peptides has been reported to reveal that a positively charged, amphipathic sequence containing at least 20 amino acids appeared to be a requirement for lytic activity in some classes of peptides. Shiba et al., "Structure-activity relationship of Lepidopteran, a self-defense peptide of *Bombyx more*," *Tetrahedron*, vol. 44, No. 3, pp.787–803 (1988). Other work has shown that smaller peptides can also be lytic. See McLaughlin et al., cited below.

Cecropins have been shown to target pathogens or compromised cells selectively, without affecting normal host cells. The synthetic lytic peptide known as S-1 (or Shiva 1) has been shown to destroy intracellular *Brucella abortus*-, *Trypanosoma cruzi*-, *Cryptosporidium parvum*-, and infectious bovine herpes virus I (IBR)-infected host cells, with little or no toxic effects on noninfected mammalian cells. See Jaynes et al., "In vitro effect of lytic peptides on normal and transformed mammalian cell lines," *Peptide Research*, vol. 2, No. 2, pp. 1–5 (1989); Wood et al., "Toxicity of a Novel Antimicrobial Agent to Cattle and Hamster cells In vitro," Proc. Ann. Amer. Soc. Anim. Sci., Utah State University, Logan, Utah. *J. Anim. Sci. (Suppl. 1)*, vol. 65, p. 380 (1987); Arrowood et al., "Hemolytic properties of lytic peptides active against the sporozoites of *Cryptosporidium parvum*," *J. Protozool.*, vol. 38, No. 6, pp. 161S–163S (1991); Arrowood et al., "In vitro activities of lytic peptides against the sporozoites of *Cryptosporidium parvum*," *Antimicrob. Agents Chemother.*, vol. 35, pp. 224–227 (1991); and Reed et al., "Enhanced in vitro growth of murine fibroblast cells and preimplantation embryos cultured in medium supplemented with an amphipathic peptide," *Mol. Reprod. Devel.*, vol. 31, No. 2, pp. 106–113 (1992).

Morvan et al., "In vitro activity of the antimicrobial peptide magainin 1 against *Bonamia ostreae*, the intrahemocytic parasite of the flat oyster *Ostrea edulis*," *Mol. Mar. Biol.*, vol. 3, pp. 327–333 (1994) reports the in vitro use of a magainin to selectively reduce the viability of the parasite *Bonamia ostreae* at doses that did not affect cells of the flat oyster *Ostrea edulis*.

Also of interest are the synthetic peptides disclosed in the following pending patent applications, peptides that have lytic activity with as few as 10–14 amino acid residues: McLaughlin et al., "Amphipathic Peptides," U.S. Pat. No. 5,789,542, issued Aug. 4, 1998; and Mark L. McLaughlin et al., "Short Amphipathic Peptides with Activity against Bacteria and Intracellular Pathogens," U.S. patent application Ser. No. 08/796,123, filed Feb. 6, 1997.

Lytic peptides such as are known generally in the art may be used in practicing the present inventions. Selective toxicity to ligand-activated cells is desirable, especially when the ligand and peptide are administered separately. Selective toxicity is less important when the ligand and peptide are linked to one another, because in that case the peptide is effectively concentrated in the immediate vicinity of cells having receptors for the ligand.

Examples of such peptides are those designated D1A21 (SEQ. ID NO. 5), D2A21 (SEQ. ID NO. 6), D5C (SEQ. ID NO. 7), and D5C1 (SEQ. ID NO. 8). These peptides and other lytic peptides suitable for use in the present invention are disclosed in Jaynes, "Methods for the Design of Amphipathic Peptides Having Enhanced Biological Activities," U.S. provisional patent application serial No. 60/027,628, filed Oct. 4, 1996.

Miscellaneous

As used in the Claims, an "effective amount" of a composition is an amount that is sufficient to induce long-term contraception or sterility in a mammal. Where appropriate in context, an "effective amount" of gonadotropic hormones is an amount sufficient to temporarily restore fertility in a mammal that has been made sterile by destruction of gonadotropic cells. As used in the Claims, the term "mammal" is intended to include both human and non-human mammals.

The complete disclosures of all references cited in this specification are hereby incorporated by reference; as are the full disclosures of U.S. provisional application No. 60/041, 009, filed Mar. 27, 1997; U.S. provisional application No. 60/057,456, filed Sep. 3, 1997; U.S. non-provisional application Ser. No. 08/869,153, filed Jun. 4, 1997; and international application PCT/US98/06114, filed Mar. 27, 1998. In the event of an otherwise irreconcilable conflict, however, the present specification shall control.

What is claimed:

1. A compound comprising: (a) a hormone domain selected from the group consisting of gonadotropin-releasing hormone, the beta subunit of luteinizing hormone, the beta subunit of chorionic gonadotropin, and analogues of these hormones; covalently linked to (b) a lytic peptide domain.

2. A compound as recited in claim 1, wherein said hormone domain is bonded directly to said lytic peptide domain, without an intermediate linking domain joining said hormone domain to said lytic peptide domain.

3. A compound as recited in claim 1, wherein said lytic peptide domain is selected from the group consisting of a cecropin peptide, a melittin peptide, a defensin peptide, a magainin peptide, a sarcotoxin peptide, and analogs of said peptides.

4. A compound as recited in claim 1, wherein said lytic peptide domain comprises hecate.

5. A compound as recited in claim 1, wherein said compound has the sequence SEQ. ID NO. 3.

6. A compound as recited in claim 1, wherein said compound has the sequence SEQ. ID NO. 4.

7. A compound as recited in claim 1, wherein said hormone domain, or said lytic peptide domain, or both comprise D-conformation amino acid residues.

8. A compound as recited in claim 7, additionally comprising a vitamin $B_{12}$ carrier domain to facilitate uptake by the intestine when the compound is administered orally.

9. A method for decreasing fertility in a mammal, comprising the consecutive steps of: (a) first, administering to the mammal an effective amount of gonadotropin-releasing hormone or an agonist of gonadotropin-releasing hormone; and (b) second, administering to the mammal an effective amount of a lytic peptide.

10. A method as recited in claim 9, wherein the hormone, or the lytic peptide, or both comprise D-conformation amino acid residues.

11. A method as recited in claim 10, wherein the compound containing D-conformation amino acid residues additionally is covalently linked a vitamin $B_{12}$ carrier domain to facilitate uptake by the intestine when the compound is administered orally.

12. A method for decreasing fertility in a mammal, comprising administering to the mammal a compound comprising: (a) a hormone domain selected from the group consisting of gonadotropin-releasing hormone, the beta subunit of luteinizing hormone, the beta subunit of chorionic gonadotropin, and analogues of these hormones; covalently linked (b) a lytic peptide domain.

13. A method as recited in claim 12, wherein the hormone domain is bonded directly to the lytic peptide domain, without an intermediate linking domain joining the hormone domain to the lytic peptide domain.

14. A method as recited in claim 12, wherein the lytic peptide domain is selected from the group consisting of a cecropin peptide, a melittin peptide, a defensin peptide, a magainin peptide, a sarcotoxin peptide, and analogs of said peptides.

15. A method as recited in claim 12, wherein the lytic peptide domain comprises hecate.

16. A method as recited in claim 12, wherein the compound has the sequence SEQ. ID NO. 3.

17. A method as recited in claim 12, wherein the compound has the sequence SEQ. ID NO. 4.

18. A method as recited in claim 9, wherein the mammal is a dog.

19. A method as recited in claim 9, wherein the mammal is a cat.

20. A method as recited in claim 9, wherein the mammal is a cow or bull.

21. A method as recited in claim 9, wherein the mammal is a pig.

22. A method as recited in claim 9, wherein the mammal is a horse.

23. A method as recited in claim 9, wherein the mammal is a sheep.

24. A method as recited in claim 9, wherein the mammal is a human.

25. A method as recited in claim 12, wherein the mammal is a dog.

26. A method as recited in claim 12, wherein the mammal is a cat.

27. A method as recited in claim 12, wherein the mammal is a cow or bull.

28. A method as recited in claim 12, wherein the mammal is a pig.

29. A method as recited in claim 12, wherein the mammal is a horse.

30. A method as recited in claim 12, wherein the mammal is a sheep.

31. A method as recited in claim 12, wherein the mammal is a human.

32. A method for selectively killing gonadotrophic cells in the pituitary of a mammal, comprising administering to the mammal: (a) an effective amount of gonadotropin-releasing hormone, and (b) an effective amount of a lytic peptide.

33. A method for selectively killing gonadotrophic cells in the pituitary of a mammal, comprising administering to the mammal an effective amount of a compound comprising a gonadotropin-releasing hormone domain covalently linked to a lytic peptide domain.

34. A method for selectively killing neurons having gonadotrophic receptors in a mammal, comprising administering to the mammal: (a) an effective amount of gonadotropin-releasing hormone, and (b) an effective amount of a lytic peptide.

35. A method for selectively killing neurons having gonadotrophic receptors in a mammal, comprising administering to the mammal an effective amount of a compound comprising a gonadotropin-releasing hormone domain covalently linked to a lytic peptide domain.

36. A method as recited in claim 9, wherein the mammal is sexually immature.

37. A method as recited in claim 12, wherein the mammal is sexually immature.

38. A compound as recited in claim 1, wherein said hormone domain comprises the beta subunit of luteinizing hormone.

39. A compound as recited in claim 1, wherein said hormone domain comprises the beta subunit of chorionic gonadotropin.

* * * * *

SEQUENCE LISTING (1) GENERAL INFORMATION:

(iii) NUMBER OF SEQUENCES: 13

(2) INFORMATION FOR SEQ ID NO: 1:

(i) SEQUENCE CHARACTERISTICS:

(A) LENGTH: 10 amino acids
        (B) TYPE: amino acid
        (D) TOPOLOGY: linear (ii) MOLECULE TYPE: peptide (ix) FEATURE:
        (A) NAME/KEY: Peptide
        (B) LOCATION: 1..10
        (D) OTHER INFORMATION: /note= "Xaa in position 1 denotes
             pyro-glutamic acid.  This sequence is GnRH."

(xi) SEQUENCE DESCRIPTION: SEQ ID NO: 1:

Xaa His Trp Ser Tyr Gly Leu Arg Pro Gly
1               5                   10

(2) INFORMATION FOR SEQ ID NO: 2:

(i) SEQUENCE CHARACTERISTICS:
        (A) LENGTH: 23 amino acids
        (B) TYPE: amino acid
        (D) TOPOLOGY: linear (ii) MOLECULE TYPE: peptide (ix) FEATURE:
        (A) NAME/KEY: Peptide
        (B) LOCATION: 1..23
        (D) OTHER INFORMATION: /note= "This sequence is hecate."

(xi) SEQUENCE DESCRIPTION: SEQ ID NO: 2:

Phe Ala Leu Ala Leu Lys Ala Leu Lys Lys Ala Leu Lys Lys Leu Ly
1               5                   10                  15

Lys Ala Leu Lys Lys Ala Leu
            20

(2) INFORMATION FOR SEQ ID NO: 3:

(i) SEQUENCE CHARACTERISTICS:
        (A) LENGTH: 33 amino acids
        (B) TYPE: amino acid
        (D) TOPOLOGY: linear (ii) MOLECULE TYPE: peptide (ix) FEATURE:
        (A) NAME/KEY: Peptide
        (B) LOCATION: 1..33
        (D) OTHER INFORMATION: /note= "This sequence is a modified
             GnRH/hecate fusion peptide."

(xi) SEQUENCE DESCRIPTION: SEQ ID NO: 3:

Gln His Trp Ser Tyr Gly Leu Arg Pro Gly Phe Ala Leu Ala Leu Ly
1               5                   10                  15

Ala Leu Lys Lys Ala Leu Lys Lys Leu Lys Lys Ala Leu Lys Lys Al
            20                  25                  30

Leu (2) INFORMATION FOR SEQ ID NO: 4:

(i) SEQUENCE CHARACTERISTICS:
        (A) LENGTH: 33 amino acids
        (B) TYPE: amino acid
        (D) TOPOLOGY: linear (ii) MOLECULE TYPE: peptide (ix) FEATURE:
        (A) NAME/KEY: Peptide
        (B) LOCATION: 1..33

(D) OTHER INFORMATION: /note= "This sequence is a
               hecate/modified GnRH fusion peptide."

(xi) SEQUENCE DESCRIPTION: SEQ ID NO: 4:

Phe Ala Leu Ala Leu Lys Ala Leu Lys Lys Ala Leu Lys Lys Leu Ly
1               5                   10                  15

Lys Ala Leu Lys Lys Ala Leu Gln His Trp Ser Tyr Gly Leu Arg Pr
            20                  25                  30

Gly (2) INFORMATION FOR SEQ ID NO: 5:

(i) SEQUENCE CHARACTERISTICS:
         (A) LENGTH: 23 amino acids
         (B) TYPE: amino acid
         (D) TOPOLOGY: linear (ii) MOLECULE TYPE: peptide (ix) FEATURE:
         (A) NAME/KEY: Peptide
         (B) LOCATION: 1..23
         (D) OTHER INFORMATION: /note= "This sequence is D1A21."

(xi) SEQUENCE DESCRIPTION: SEQ ID NO: 5:

Phe Ala Phe Ala Phe Lys Ala Phe Lys Lys Ala Phe Lys Lys Phe Ly
1               5                   10                  15

Lys Ala Phe Lys Lys Ala Phe
            20

(2) INFORMATION FOR SEQ ID NO: 6:

(i) SEQUENCE CHARACTERISTICS:
         (A) LENGTH: 23 amino acids
         (B) TYPE: amino acid
         (D) TOPOLOGY: linear (ii) MOLECULE TYPE: peptide (ix) FEATURE:
         (A) NAME/KEY: Peptide
         (B) LOCATION: 1..23
         (D) OTHER INFORMATION: /note= "This sequence is D2A21."

(xi) SEQUENCE DESCRIPTION: SEQ ID NO: 6:

Phe Ala Lys Lys Phe Ala Lys Lys Phe Lys Lys Phe Ala Lys Lys Ph
1               5                   10                  15

Ala Lys Phe Ala Phe Ala Phe
            20

(2) INFORMATION FOR SEQ ID NO: 7:

(i) SEQUENCE CHARACTERISTICS:
         (A) LENGTH: 27 amino acids
         (B) TYPE: amino acid
         (D) TOPOLOGY: linear (ii) MOLECULE TYPE: peptide (ix) FEATURE:
         (A) NAME/KEY: Peptide
         (B) LOCATION: 1..27
         (D) OTHER INFORMATION: /note= "This sequence is D5C."

(xi) SEQUENCE DESCRIPTION: SEQ ID NO: 7:

Lys Arg Lys Arg Ala Val Lys Arg Val Gly Arg Arg Leu Lys Lys Le
1               5                   10                  15

```
Ala Arg Lys Ile Ala Arg Leu Gly Val Ala Phe
            20                  25
```

(2) INFORMATION FOR SEQ ID NO: 8:

(i) SEQUENCE CHARACTERISTICS:
        (A) LENGTH: 37 amino acids
        (B) TYPE: amino acid
        (D) TOPOLOGY: linear (ii) MOLECULE TYPE: peptide (ix) FEATURE:
        (A) NAME/KEY: Peptide
        (B) LOCATION: 1..37
        (D) OTHER INFORMATION: /note= "This sequence is D5C1."

(xi) SEQUENCE DESCRIPTION: SEQ ID NO: 8:

```
Lys Arg Lys Arg Ala Val Lys Arg Val Gly Arg Arg Leu Lys Lys Le
1               5                   10                  15

Ala Arg Lys Ile Ala Arg Leu Gly Val Ala Lys Leu Ala Gly Leu Ar
            20                  25                  30

Ala Val Leu Lys Phe
            35
```

(2) INFORMATION FOR SEQ ID NO: 9:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (ix) FEATURE:
        (A) NAME/KEY: Peptide
        (B) LOCATION: 1..10
        (D) OTHER INFORMATION: /note= "This sequence is a modified
            GnRH."

(xi) SEQUENCE DESCRIPTION: SEQ ID NO: 9:

```
Gln His Trp Ser Tyr Gly Leu Arg Pro Gly
1               5                   10
```

(2) INFORMATION FOR SEQ ID NO: 10:

(i) SEQUENCE CHARACTERISTICS:

(xi) SEQUENCE DESCRIPTION: SEQ ID NO: 10:

This sequence is intentionally skipped (2) INFORMATION FOR SEQ ID NO: 11:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (ix) FEATURE:
        (A) NAME/KEY: Peptide
        (B) LOCATION: 1..15
        (D) OTHER INFORMATION: /note= "This sequence is bLH."

(xi) SEQUENCE DESCRIPTION: SEQ ID NO: 11:

```
Ser Tyr Ala Val Ala Leu Ser Cys Gln Cys Ala Leu Cys Arg Arg
1               5                   10                  15
```

(2) INFORMATION FOR SEQ ID NO: 12:

(i) SEQUENCE CHARACTERISTICS:
        (A) LENGTH: 38 amino acids
        (B) TYPE: amino acid
        (D) TOPOLOGY: linear (ii) MOLECULE TYPE: peptide (ix) FEATURE:
        (A) NAME/KEY: Peptide
        (B) LOCATION: 1..38
        (D) OTHER INFORMATION: /note= "This sequence is a
            hecate-bLH fusion peptide."

(xi) SEQUENCE DESCRIPTION: SEQ ID NO: 12:

```
Phe Ala Leu Ala Leu Lys Ala Leu Lys Lys Ala Leu Lys Lys Leu Ly
1               5                   10                  15

Lys Ala Leu Lys Lys Ala Leu Ser Tyr Ala Val Ala Leu Ser Cys Gl
            20                  25                  30

Cys Ala Leu Cys Arg Arg
        35
```

(2) INFORMATION FOR SEQ ID NO: 13:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (ix) FEATURE:
        (A) NAME/KEY: Peptide
        (B) LOCATION: 1..10
        (D) OTHER INFORMATION: /note= "Xaa in position 1 denotes
            pyro-glutamic acid. Xaa in position 6 denotes
            D-lysine. This sequence is D-Lys-6 GnRH."

(xi) SEQUENCE DESCRIPTION: SEQ ID NO: 13:

```
Xaa His Trp Ser Tyr Xaa Leu Arg Pro Gly
1               5                   10
```